United States Patent [19]
Boudjema

[11] Patent Number: 5,827,297
[45] Date of Patent: Oct. 27, 1998

[54] DEVICE FOR TRANSPLANTING SMALL DIAMETER HAIR GRAFTS

[75] Inventor: Pascal J. Boudjema, Paris, France

[73] Assignee: Medicamat S.A., Malakoff, France

[21] Appl. No.: 403,929

[22] PCT Filed: Sep. 30, 1993

[86] PCT No.: PCT/FR93/00955

§ 371 Date: Mar. 21, 1995

§ 102(e) Date: Mar. 21, 1995

[87] PCT Pub. No.: WO94/07433

PCT Pub. Date: Apr. 14, 1994

[30] Foreign Application Priority Data

Oct. 1, 1992 [FR] France ................................. 92 12105

[51] Int. Cl.⁶ .................................................. A61B 17/50
[52] U.S. Cl. ........................... 606/133; 604/22; 606/131; 606/167; 606/170; 600/565; 600/564
[58] Field of Search ..................... 606/187, 133, 606/131, 36, 42, 180, 184; 604/22; 600/564, 565, 566, 568, 570, 571

[56] References Cited

U.S. PATENT DOCUMENTS

| | | | |
|---|---|---|---|
| Re. 34,556 | 3/1994 | Sjostrom et al. | 606/180 |
| 3,219,022 | 11/1965 | Hagemeyer | 606/187 |
| 3,589,363 | 6/1971 | Banko | 604/22 |
| 3,618,611 | 11/1971 | Urban | 606/170 |
| 3,867,942 | 2/1975 | Bellantoni et al. | 606/180 |
| 4,160,453 | 7/1979 | Miller | 606/187 |
| 4,476,864 | 10/1984 | Tezel | 606/131 |
| 4,838,853 | 6/1989 | Parisi | 604/22 |
| 4,867,155 | 9/1989 | Isaacson | 128/305 |
| 5,019,035 | 5/1991 | Missirlian et al. | 604/22 |
| 5,275,609 | 1/1994 | Pingleton et al. | 606/170 |
| 5,417,683 | 5/1995 | Shiao | 606/1 |
| 5,520,634 | 5/1996 | Fox et al. | 606/180 |

FOREIGN PATENT DOCUMENTS

A0237818  9/1987  European Pat. Off. .
WOA9113596 9/1991  WIPO .

*Primary Examiner*—Richard J. Apley
*Assistant Examiner*—Justine R. Yu
*Attorney, Agent, or Firm*—Christie, Parker & Hale, LLP

[57] ABSTRACT

A device for transplanting small diameter hair grafts using a hand-held cutting instrument having a body holding the tool, a rotary cylindrical tool and a drive assembly capable of driving the tool in rotation with respect to the body. The tool has a hollow end for cutting a graft. The cylindrical tool is a hollow needle with an axial through bore of the same diameter as the hollow cutting end to which it forms an extension. The device extracts the graft by sucking it up through the axial bore of the needle.

13 Claims, 5 Drawing Sheets

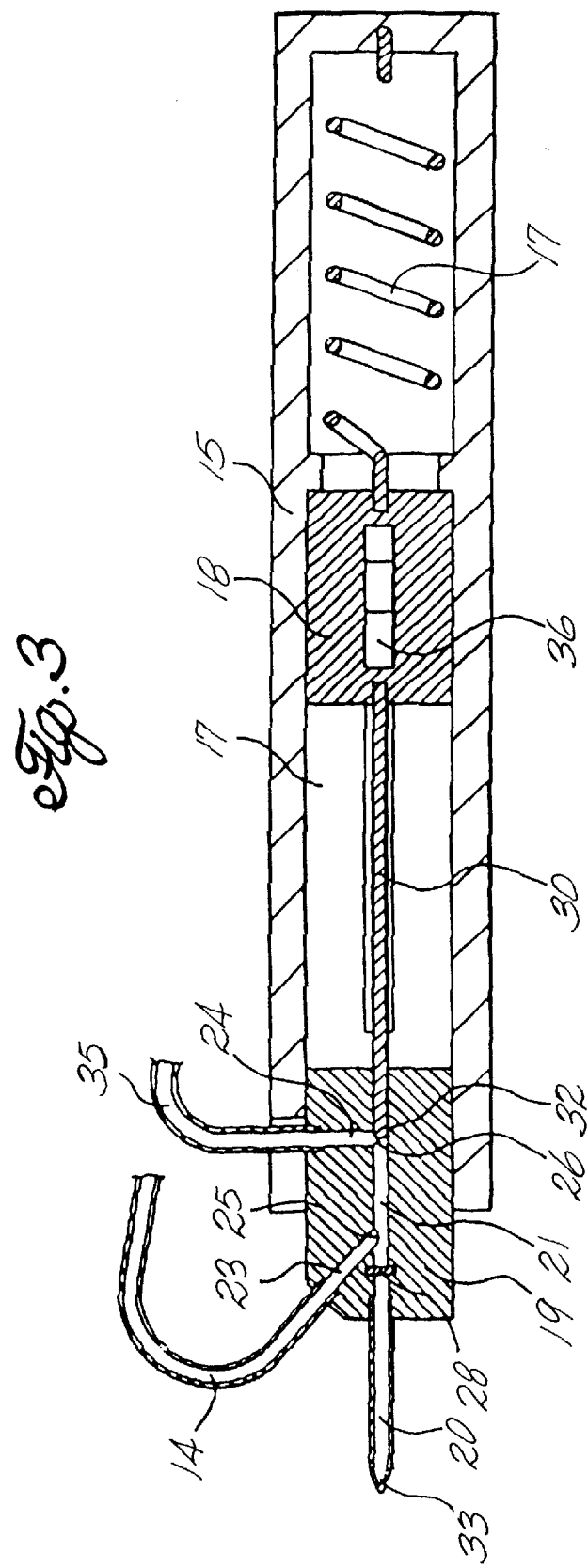

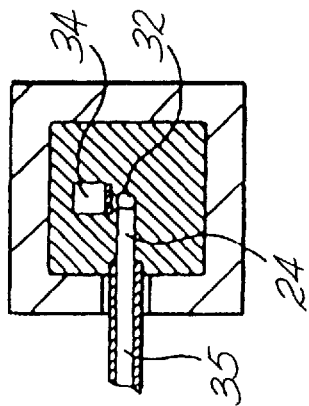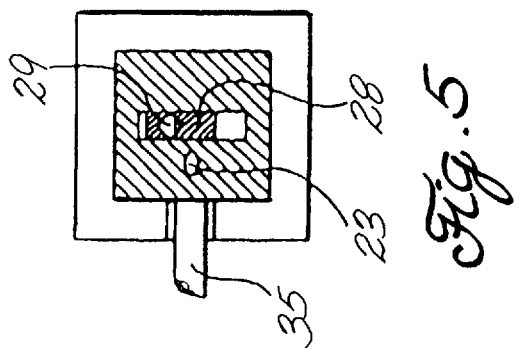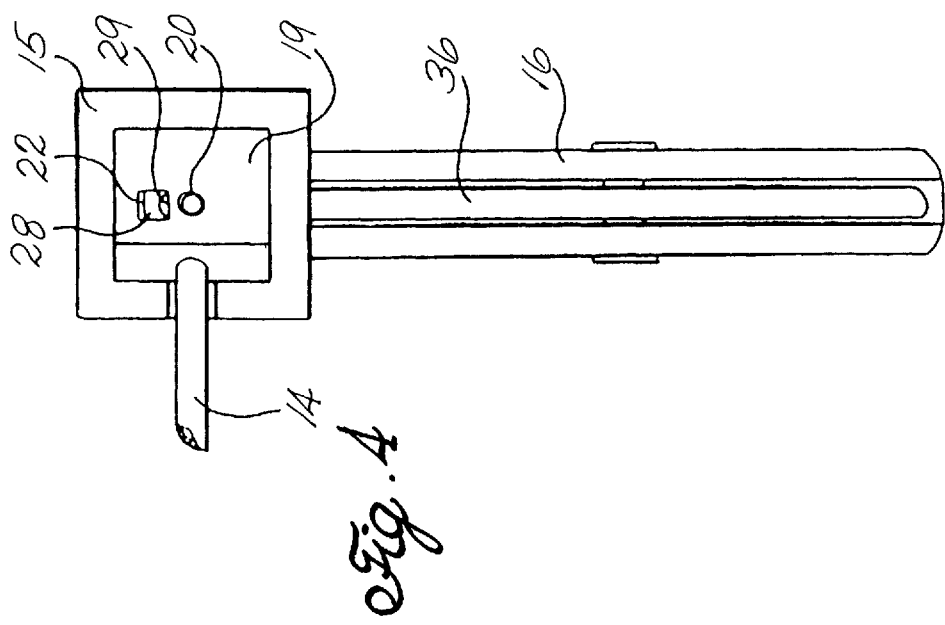

DEVICE FOR TRANSPLANTING SMALL DIAMETER HAIR GRAFTS

BACKGROUND OF THE INVENTION

The present invention relates to a device for transplanting small-diameter hair grafts into the scalp, comprising a surgical cutting instrument including a rotary cylindrical tool provided with a cylindrical hollow drilling tip for cutting out the grafts at one end.

It finds one particularly important, although not exclusive, application in the field of the surgical treatment of baldness by the grafting of natural hairs and, more particularly, in the field of micrografting.

The treatment of baldness by hair transplantation, called the graft technique, consists in transplanting, within the same individual, part of the roots of his hairs located in the crown (still covered with hair) into the bald areas.

The grafts are cylindrical cutaneous fragments obtained by circular cutting-out of the skin with the aid of a surgical cutting instrument as defined hereinabove.

The cutaneous fragments thus cut out along their periphery are, secondly, extracted one by one with the aid of tweezers and scissors and then, thirdly, are reimplanted one by one into respective receiver sites prepared beforehand.

The known surgical techniques cut out grafts of smaller and smaller diameter, for example micrografts, of approximately 1.5 mm in diameter and 6 mm in length, so as to guarantee an esthetic result of high quality.

Unfortunately, these micrografts often remain blocked at the bottom of the drilling tip because of their very small diameter, this requiring them to be manually dislodged with the aid of microtweezers.

Independently of this drawback, the micrografts cut out must be gripped one by one with the aid of microtweezers, detached from the scalp with scissors and then placed in a preserving solution so as to prevent them from drying out during the preparation of the receiver sites into which they are finally placed, manually, one by one with the aid of microtweezers.

These painstaking and very delicate operations run the risk of traumatizing the micrografts and considerably lengthen the operating times.

SUMMARY OF THE INVENTION

The object of the present invention is to eliminate the drawbacks mentioned hereinabove by providing a device and a method preferable to those known previously, especially by enabling micrografts of excellent quality to be extracted rapidly and then subsequently reimplanted immediately or almost immediately after their extraction, inexpensively and in a manner which is both simple and easy to implement.

For this purpose, the invention essentially provides a device for transplanting small-diameter hair grafts, comprising a hand-held cutting instrument including a tool-holding body, a rotary cylindrical, tool and a driving assembly suitable for driving the tool in rotation with respect to the body, the tool being provided with a hollow end for cutting out a graft, characterized in that the cylindrical tool is a hollow needle pierced through by an axial bore of the same diameter as the hollow cutting-out end which it extends. The needle is preferably removably mounted with respect to the body. The device also includes means for extracting the graft by sucking up said graft through the axial bore of the needle.

In one embodiment, the extraction means comprises a collector hose, of the same internal diameter or substantially the same internal diameter as the bore of the needle, means for connecting the collector hose in a sealed manner to the rear end of the rotary needle, and means for creating a vacuum in the bore of the needle and in the collector hose, said collector hose being connected to a container for intermediate storage of the extracted graft.

In one embodiment, the connection means comprises a conduit integral with the body and axially connected on one side to the hose, the rear end of the needle rotationally interacting in a sealed manner with the other end of said conduit, said conduit comprising an internal bore of the same internal diameter as the internal diameter of the collector hose.

In addition, the device may also include a hand-held apparatus for implanting the extracted graft, the apparatus comprising a 'body, the container for intermediate graft storage, a second hollow needle, for reimplantation, pierced through by a bore of the same diameter as the bore of the first hollow needle, and means for inserting the graft into the scalp via said second hollow needle from the intermediate container. The insertion means is preferably pneumatic or manual.

Preferably the container for intermediate storage of the graft comprises a first channel axially connected to the second hollow needle. The first channel is cylindrical, of the same diameter or substantially of the same diameter as the hose with which it is obliquely connected. The first channel is straight and the means for inserting the graft into the scalp comprise a first piston suitable for interacting with the internal bore of the second needle and designed to push the graft through the second needle. The oblique connection has a decreasing slope directed from the front of the second needle towards its rear and lying between of the order of 10° and of the order of 60°.

In one embodiment, the apparatus includes means for butting up against the scalp, these being designed to withdraw the second needle after insertion and deposition of the graft in the scalp. The butting means include a second channel parallel to the first channel and a second piston suitable for coming to bear on the scalp, the second piston being integral with the first piston.

Many advantages and characteristics of the present invention will become apparent in the course of the detailed description which follows, given with regard to the appended drawings which provide, by way of explanation but with no limitation implied, an embodiment in accordance with the invention.

DESCRIPTION OF THE DRAWINGS

FIG. 3 is a horizontal longitudinal section along the line 3—3 of FIG. 2;

FIG. 4 is a front view of the reimplantation apparatus of FIG. 2;

FIG. 5 is a cross section along the line 5—5 of FIG. 2;

FIG. 6 is a cross section along the line 6—6 of FIG. 2;

DETAILED DESCRIPTION

Figure 1:
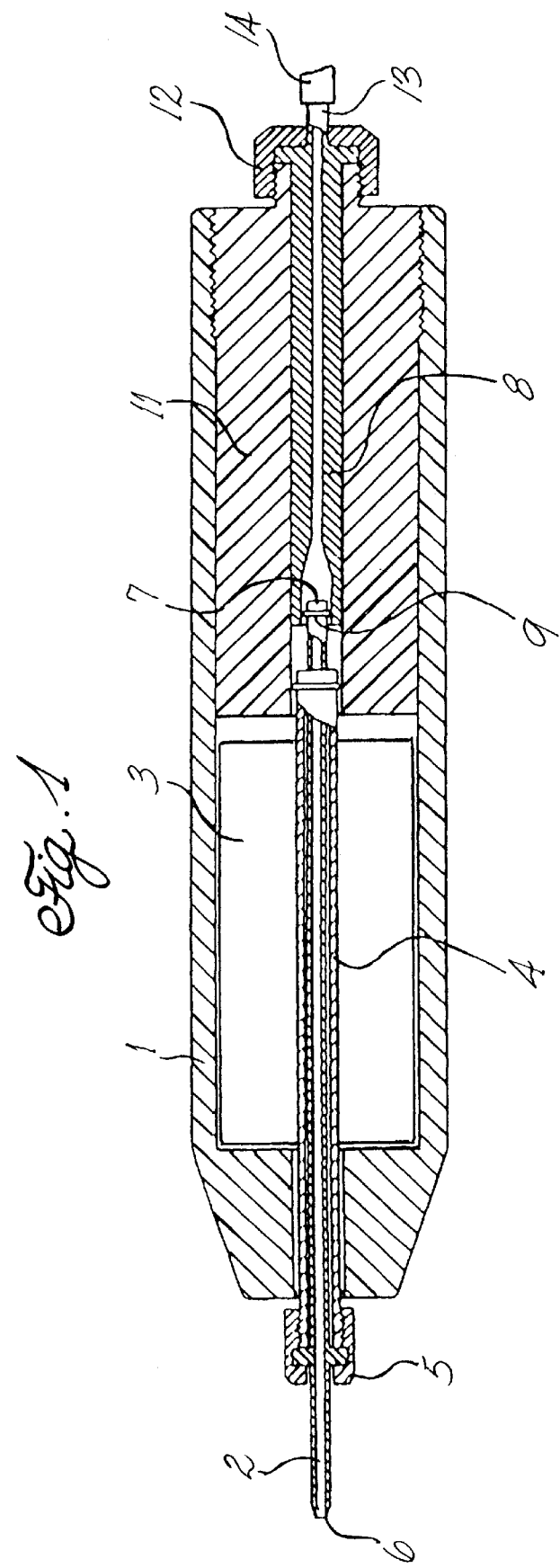
FIG. 1 is a longitudinal section of the cutting instrument forming part of the device according to one embodiment of the invention.
Figure 2:
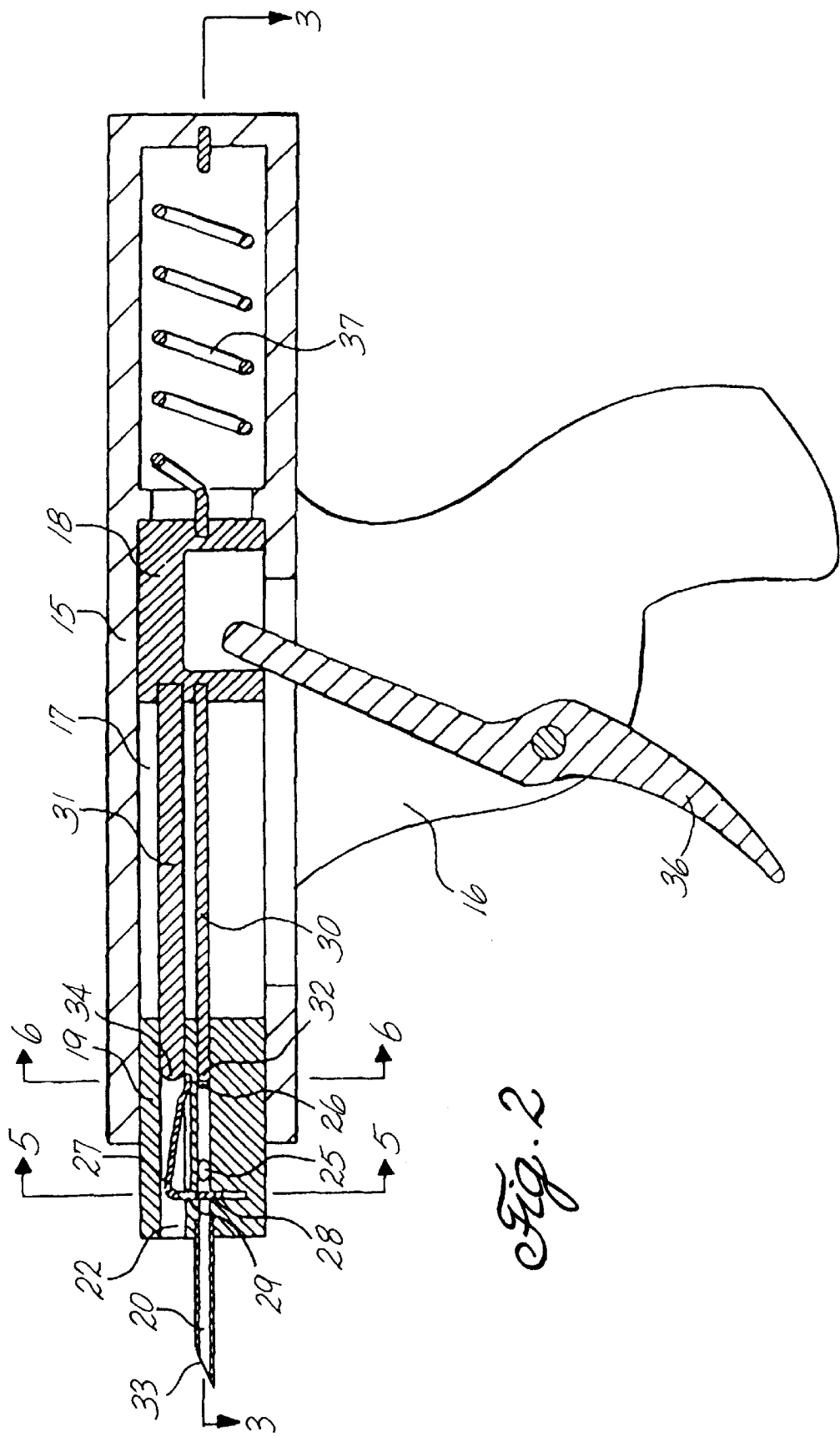
FIG. 2 is a vertical longitudinal section of a reimplantation apparatus, in the form of a gun, according to one embodiment of the invention.

FIG. 1 shows that the surgical cutting instrument according to the invention consists of an elongate body 1 of cylindrical shape (the dimensions of which may be approximately 12 cm in length and 3 cm in diameter) acting as a part held in the hand, in which body is arranged, along its axis, a rigid, straight, cylindrical, hollow metal needle 2 which has a very thin wall and a very small inside diameter (approximately 1.5 mm) and is suitable for being set in axial rotary movement by means of a motor 3 having a hollow drive shaft 4 whose inside diameter is very slightly greater than the outside diameter of the needle 2.

The needle 2 is firmly held in the hollow shaft 4 by a lock nut 5 arranged at the front and at the end of the body 1.

The front end 6 of the needle 2, extending beyond the head of the part held in the hand by a few centimeters, has a cross section whose bevelled and cutting circular edge acts as the end for drilling in the scalp. The needle 2 is extended at its rear end 7, within the part held in the hand, by a cylindrical, straight, hollow, fixed, metal needle 8 (collecting needle) arranged along its axis, having a slightly greater diameter in the region of the junction with the rear end of the needle 2 which is fitted into it by a few millimeters and hermetically sealed by means of an airtight lipped ring or seal 9.

The fixed needle 8 is arranged in the central axial bore 10 of a cylindrical body 11 screwed onto the rear of the body 1. This needle is fixed to the cylindrical body 11 by a lock nut 12 arranged at the rear and at the end of the body 1.

A hose 14 made of soft plastic (collector hose), of the same inside diameter as that of the needle 8 and of length sufficient to be connected to the reimplantation gun, is joined onto the rear end 13 of the needle 8 on the outside of the part held in the hand.

FIGS. 2 to 6 show that the reimplantation device consists of a part held in the hand, this having the shape of a gun with a body 15 and a stock 16.

The body of the gun consists of a hollow cylinder 17 inside which a piston 18 slides with a horizontal translational movement.

Fitted into the front end of the cylinder 17 is a fixed member 19 of a shape substantially identical to that of the piston (reimplantation head), extended at the front and on the outside by a hollow needle 20 (reimplantation needle of approximately 3 to 4 cm in length).

The reimplantation head 19 is rendered hollow, along its axis and over its entire length, by two mutually parallel channels; a central longitudinal channel 21 (channel for collecting the graft) or first channel; and a paracentral longitudinal channel 22 or second channel.

The central channel 21 is cylindrical and straight, of the same diameter as the inside diameter of the reimplantation needle 20 by which it is extended at the front.

Two small straight cylindrical channels 23 and 24 join laterally into the central channel 21.

The front channel 23 (graft inlet channel), of the same diameter as the central channel 21, joins into the latter at a sufficiently open angle at the rear, in such a way that a graft arriving via the front lateral channel 23 can easily be positioned into the central channel 21, without being impaired.

The rear lateral channel 24 (suction channel) joins perpendicularly into the central channel 21.

The rear lateral channel 24 is connected on the outside to a vacuum source, known per se, via a hose 35 made of soft plastic.

The distance separating the orifices where the lateral channels 23 and 24 join into the central channel 21 must be greater than the length of a graft (approximately 6 mm).

Arranged within the paracentral channel 22 is a springy member 27 of the spring-leaf type, extended at its front part by a vertical portion 28 acting as a valve which, in the rest position, hermetically obstructs the central channel 21, in front of the adjoining orifice 25.

An opening 29 is arranged within the vertical portion 28 of the device 27 in such a way that, when the vertical portion 28 is lowered (by a means which we will describe later), this opening 29 can bring the central channel 21 into free communication with the needle 20.

The piston 18 consists of a component which can move in the cylinder 17, this component being extended at the front by two mutually parallel, longitudinal, straight, rigid rods of the same length - a central rod 30 and a paracentral rod 31. The central rod 30 (reimplantation rod), of cylindrical shape, is arranged along the axis of the central channel 21 in which it is engaged at its rear part.

Likewise, the paracentral rod 31 (guide rod) is arranged along the axis of the paracentral channel 22 in which it is engaged at its rear part.

The diameter and the length of the central rod 30 are such that, when the piston 18 is moved forward into the cylinder 17, it can slide freely and hermetically over the entire length of the central channel 21 and of the needle 20, and such that its front end 32 can project slightly from the end 33 of the needle 20, at the end of the stroke.

The rest distance separating the piston 18 from the reimplantation head 19 is such that the central rod 30 is already engaged in the central channel 21 and such that its front end 32 partially obstructs the adjoining orifice 26 of the rear lateral channel 24.

In the same manner, the paracentral rod 31 is arranged in such a way that, at rest, it is already engaged in the paracentral channel 22 and without acting on the spring leaf 27 and such that, when it is moved forward parallel to and conjointly with the central rod 30, its front end 34 lowers the leaf 27 and its vertical portion 28, and, thereby, brings the central channel 21 into communication with the needle 20 via the opening 29.

At the end of the stroke, the front end 34 of the rod 31 is also designed to serve as a stop against the skin. The forward motion of the piston 18 in the cylinder 17 is achieved manually by a lever or trigger 36. The return of the piston 18 to the rear, into the rest position, is achieved by the action of a spring 37.

Figure 7:
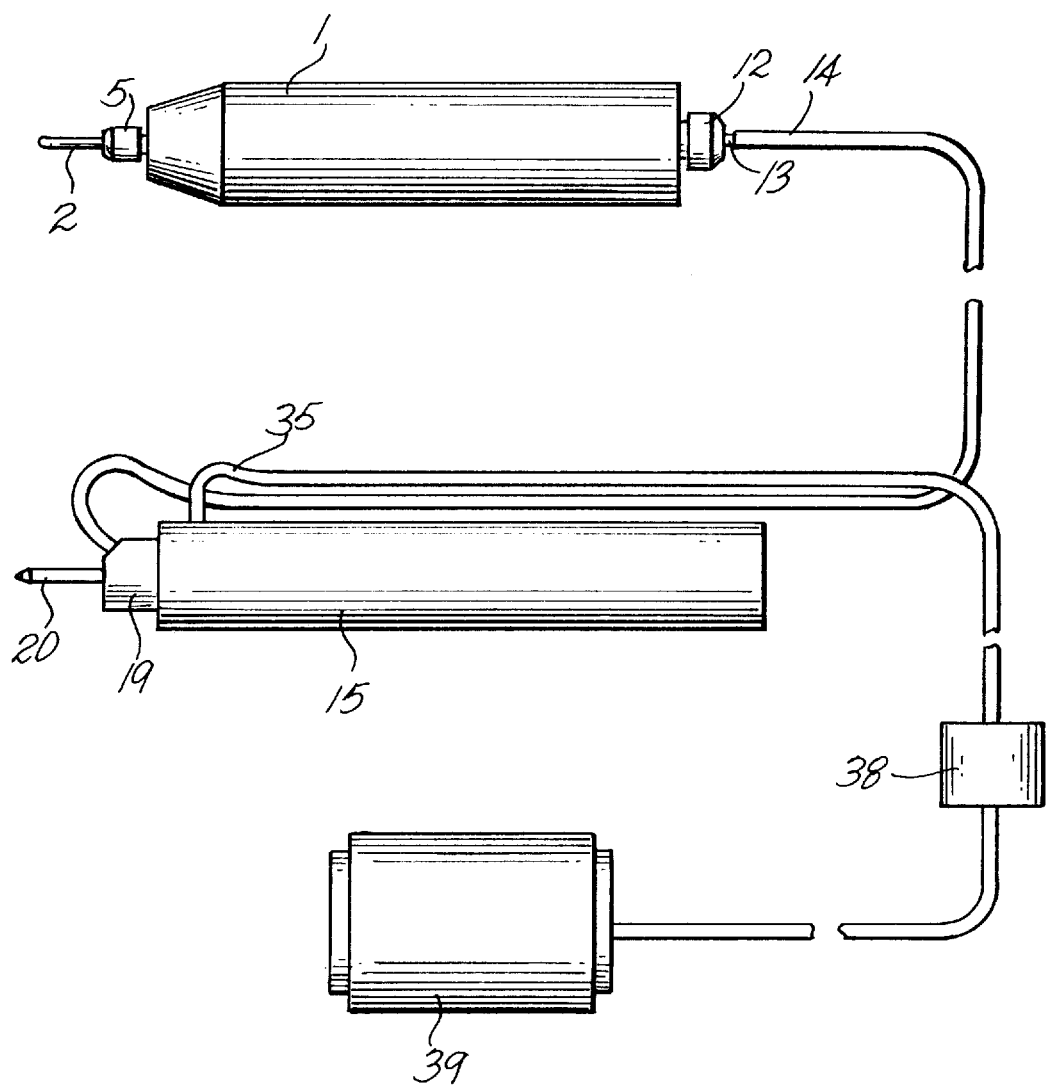
FIG. 7 is a view depicting the connections between the surgical cutting instrument and the reimplantation apparatus with the control and vacuum-creating device.

FIG. 7 shows that the vacuum may be transmitted as required into the reimplantation gun and into the cutting instrument by means of a control device 38 connected to the vacuum pump 39.

In regard to the surgical cutting instrument according to the invention, although an electric motor has been depicted as the source of driving force for the drilling needle, it is possible to use a pneumatic motor or a vacuum motor. The body of the cutting instrument may be made of a rigid high-density plastic or of metal (aluminum).

In regard to the reimplantation device, although the motion of the piston 18 in the cylinder 17 has been depicted as a force exerted by a person on a trigger 36, it is possible, for example, to use a source of pneumatic force.

The body 15 of the reimplantation gun may advantageously be made of aluminum. The reimplantation head 19 may be made of metal (aluminum or stainless steel) or of a rigid transparent plastic such as methylmethacrylate.

The spring-type device 27 may be made of metal or of rigid plastic. The rods 30 and 31 may be made of steel or of rigid high-density plastic. The hoses 14 and 35 may, for example, be made of polyethylene.

Although the reimplantation head 19 and the piston 18 have been depicted with a parallelepipedal shape in the drawings, it is, of course, also possible, for example, to design them with a cylindrical shape. Likewise, although the paracentral channel 22, in which the rod 31 slides, has been depicted with a square section in the drawings, it is possible to design it with a cylindrical shape. The end 33 of the reimplantation needle 20 may be bevelled or have a straight section.

The device according to the invention operates as follows.

It may require the participation of two operators: an extractor holding the surgical cutting instrument; and an implanter holding the reimplantation gun.

The surgical cutting instrument is switched on, whereas the vacuum is switched off.

The drilling needle is inserted into the scalp in the region of the crown to a depth (approximately 6 mm) sufficient to encompass one to a few hair roots. The vacuum is then switched on by means of the control device 38, which has the purpose of sucking up, in a fraction of a second, the cutaneous graft, the dimensions of which approximate 1.5 mm in diameter and 6 mm in length, which will travel respectively inside the needle 2, in the collecting needle 8, the collecting hose 14 and the side channel 23, and will complete its travel, in the central channel 21, by butting up against the end 32 of the reimplantation rod 30 within the reimplantation gun. The vacuum is then switched off.

The implanter inserts the reimplantation needle 20 into the bottom of the receiver cutaneous orifice, of diameter and depth substantially identical to the graft, prepared beforehand within the bald area.

The implanter then actuates the gun, moving the piston 18 forward in the cylinder 17. The graft is then pushed forward into the central channel 21 via the end 32 of the rod 30.

At the same time, the paracentral rod 31 lowers the device 27 into the channel 22, bringing the graft in front into communication with the needle 20 via the opening 29, The graft then travels right to the end 33 of the needle 20. The end 34 of the paracentral rod 31, located at the same height as the end 32 of the reimplantation rod 30 then butting up against the cutaneous surface in the region of the orifice in which the needle 20 lies, will cause the reimplantation head 19 to move back and cause, at the same time, the needle 20 to be withdrawn simultaneously, the consequence of this being that the graft is left in place in its receiver orifice. The operation is then repeated in the same manner in the same sequence for each graft.

I claim:

1. A device for transplanting small-diameter hair grafts, comprising: a hand-held cutting instrument, the instrument comprising:

a tool-holding body, a rotary cylindrical tool comprising a hollow needle having an axial bore extending therethrough, said tool having an opening at an end concentric with the axial bore for cutting out a graft, the opening having a diameter substantially equal to a diameter of the axial bore of the needle, a motor assembly suitable for driving said tool in rotation with respect to said body, and means for extracting the graft by sucking up said graft through the axial bore of the needle, said extraction means comprising a container for intermediate storage of the extracted graft and a collector hose for passing the extracted graft from the axial bore of the needle to said container.

2. The device of claim 1 wherein said extraction means comprises means for connecting said collector hose in a sealed manner to a rear end of the needle, and wherein said extraction means further comprises means for creating a vacuum in the axial bore of the needle and in the collector hose.

3. The device of claim 2 wherein said connection means comprises a conduit having an internal bore with a diameter at one end substantially equal to an inside diameter of the collector hose, said conduit being connected at said one end to one side of the hose, and rotationally interacting at another end with the needle in the sealed manner.

4. The device as in claim 1, 2, or 3 wherein said needle is removably mounted with respect to the body.

5. A device for transplanting small-diameter hair grafts, comprising;

a hand-held cutting instrument, the instrument comprising, a tool-holding body, a rotary cylindrical tool comprising a first hollow needle having a first axial bore extending therethrough, said tool having an opening at an end concentric with the first axial bore for cutting out a graft, the opening having a diameter substantially equal to a diameter of the first axial bore, and a motor assembly suitable for driving said tool in rotation with respect to said body; means for extracting the graft from the first axial bore; a hand-held apparatus for implanting the extracted graft, said apparatus comprising, a second body, a second hollow needle extending from said second body and having a second axial bore extending therethrough for reimplantation, said second axial bore having a diameter substantially equal to the diameter of the first axial bore, a container for intermediate storage of the extracted graft, and means for inserting the extracted graft intermediately stored in the container into a scalp via said second hollow needle; and a collector hose for passing the extracted graft from the first axial bore to said container.

6. The device of claim 5 wherein the container comprises a first channel axially connected to the second hollow needle.

7. The device of claim 6 wherein the first channel is cylindrical and has a diameter substantially equal to an inside diameter of the hose, the first channel being obliquely connected to the hose.

8. The device of claim 7 wherein the inserting means comprises a first piston for pushing said graft through the second axial bore of the second needle.

9. The device of claim 8 wherein the hand-held apparatus further comprises means for butting up against the scalp, said butting means being adapted to withdraw the second needle after insertion of the graft in the scalp and comprising a second channel substantially parallel to the first channel, and a second piston for bearing on the scalp, the second piston being integral with the first piston.

10. The device of claim 7 wherein the oblique connection between the hose and a portion of the second hollow needle extending from the body is substantially between 10° and 60°.

11. The device of claim 5 wherein the insertion means is pneumatic.

12. The device of claim 5 wherein the insertion means is manual.

13. The device of claim 5 wherein the hand-held apparatus further comprises means for butting up against the scalp, said butting means being adapted to withdraw the second needle after insertion of the graft in the scalp.

* * * * *